United States Patent
Groenendaal et al.

(10) Patent No.: US 11,857,308 B2
(45) Date of Patent: Jan. 2, 2024

(54) SYSTEM AND METHOD FOR RESPIRATORY MONITORING OF A SUBJECT

(71) Applicant: Stichting IMEC Nederland, Eindhoven (NL)

(72) Inventors: Willemijn Groenendaal, Leuven (BE); Ruben De Francisco Martin, Leuven (BE)

(73) Assignee: STICHTING IMEC NEDERLAND, Eindhoven (NL)

(*) Notice: Subject to any disclaimer, the term of this patent is extended or adjusted under 35 U.S.C. 154(b) by 244 days.

(21) Appl. No.: 16/271,147

(22) Filed: Feb. 8, 2019

(65) Prior Publication Data
US 2019/0246952 A1 Aug. 15, 2019

(30) Foreign Application Priority Data
Feb. 9, 2018 (EP) .................................. 18155993

(51) Int. Cl.
*A61B 5/08* (2006.01)
*A61B 5/087* (2006.01)
(Continued)

(52) U.S. Cl.
CPC ............ *A61B 5/0809* (2013.01); *A61B 5/053* (2013.01); *A61B 5/0535* (2013.01); *A61B 5/087* (2013.01);
(Continued)

(58) Field of Classification Search
CPC ........ A61B 2562/046; A61B 2562/043; A61B 2562/04; A61B 5/7282; A61B 5/7275;
(Continued)

(56) References Cited

U.S. PATENT DOCUMENTS

| 3,026,868 A | * | 3/1962 | Weinberg ............... A61B 5/087 346/33 ME |
| 4,289,142 A | * | 9/1981 | Kearns ............... A61B 5/02455 600/536 |

(Continued)

FOREIGN PATENT DOCUMENTS

| EP | 2215966 A2 | 11/2010 |
| JP | 2010-183980 A | 8/2010 |

(Continued)

OTHER PUBLICATIONS

Houtveen, J H. et al., "Validation of the signal using multilevel analysis," International Journal of Psychophysiology, Elsevier, Amsterdam, NL, vol. 59, No. 2, Feb. 1, 2006, pp. 97-106.

*Primary Examiner* — Matthew Kremer
(74) *Attorney, Agent, or Firm* — MOSER TABOADA

(57) ABSTRACT

A system for respiratory monitoring of a subject comprises: a bioimpedance measurement sensor, which is configured for arrangement in relation to the subject for acquiring a bioimpedance signal; a processing unit, which is configured to receive the acquired bioimpedance signal and receive a reference signal, the reference signal representing a respiratory effort of the subject or a respiratory airflow at a time of bioimpedance signal acquirement, the processing unit being further configured to divide the bioimpedance signal into an effort component representing a respiratory effort of the subject and a flow component representing a respiratory airflow of the subject based on the received bioimpedance signal and the received reference signal.

17 Claims, 4 Drawing Sheets

(51) Int. Cl.
  *A61B 5/053* (2021.01)
  *A61B 5/0535* (2021.01)
  *A61B 5/00* (2006.01)

(52) U.S. Cl.
  CPC .......... *A61B 5/0826* (2013.01); *A61B 5/6823* (2013.01); *A61B 5/7278* (2013.01); *A61B 2562/04* (2013.01)

(58) Field of Classification Search
  CPC ... A61B 5/7271; A61B 5/7278; A61B 5/6813; A61B 5/6823; A61B 5/087; A61B 5/05; A61B 5/0535; A61B 5/0531; A61B 5/053; A61B 5/0826; A61B 5/0816; A61B 5/0806; A61B 5/0803; A61B 5/08; A61B 5/0809
  See application file for complete search history.

(56) References Cited

U.S. PATENT DOCUMENTS

| | | | | |
|---|---|---|---|---|
| 4,630,614 | A | | 12/1986 | Atlas |
| 10,869,619 | B2 | * | 12/2020 | Hoskuldsson ......... A61B 5/087 |
| 2007/0032733 | A1 | * | 2/2007 | Burton ................. A61B 5/7264 600/509 |
| 2008/0319277 | A1 | * | 12/2008 | Bradley ................. A61B 7/003 600/301 |
| 2010/0130873 | A1 | * | 5/2010 | Yuen .................... A61B 5/0022 600/484 |
| 2010/0204601 | A1 | | 8/2010 | Masuo |
| 2010/0324398 | A1 | * | 12/2010 | Tzyy-Ping ......... A61B 5/14532 600/365 |
| 2011/0004081 | A1 | * | 1/2011 | Addison .................. A61B 5/08 600/538 |
| 2011/0197885 | A1 | * | 8/2011 | Wondka ................ A61B 5/087 128/204.22 |
| 2012/0071730 | A1 | * | 3/2012 | Romero ................. A61B 5/361 600/509 |
| 2013/0172720 | A1 | | 7/2013 | Yamamori |
| 2015/0105632 | A1 | * | 4/2015 | Melker ................ A61B 5/0836 128/204.23 |
| 2015/0224307 | A1 | * | 8/2015 | Bolea ................... A61N 1/3611 607/42 |
| 2016/0367184 | A1 | * | 12/2016 | Lim ....................... G16H 50/30 |
| 2017/0000420 | A1 | * | 1/2017 | Meftah ................ A61B 5/0538 |
| 2018/0020931 | A1 | * | 1/2018 | Shusterman ......... A61N 1/3627 600/483 |
| 2018/0049678 | A1 | * | 2/2018 | Hoskuldsson ....... A61B 5/6823 |
| 2018/0344194 | A1 | * | 12/2018 | Eger ...................... A61B 5/091 |
| 2019/0298997 | A1 | * | 10/2019 | Valvano ............... A61B 5/4836 |

FOREIGN PATENT DOCUMENTS

| | | | | |
|---|---|---|---|---|
| JP | 2016-179187 A | | 10/2016 | |
| WO | WO-2004112606 A1 | | 12/2004 | |
| WO | WO-2010149951 A1 | * | 12/2010 | ......... A61B 5/02416 |
| WO | WO 2012/021900 A1 | | 2/2012 | |

* cited by examiner

SYSTEM AND METHOD FOR RESPIRATORY MONITORING OF A SUBJECT

CROSS-REFERENCE TO RELATED APPLICATIONS

This application claims priority to EPC Application No. 18155993.1, filed on 9 Feb. 2018, which is incorporated herein by reference in its entirety

TECHNICAL FIELD

The present inventive concept relates to a system and a method for respiratory monitoring of a subject. In particular, the present inventive concept relates to respiratory monitoring based on a bioimpedance signal.

BACKGROUND

Bioimpedance signals are of increasing interest to use for monitoring of health of a subject. A bioimpedance signal may be modulated e.g. by breathing of a subject, and the bioimpedance signal may therefore be used for respiratory monitoring of the subject. This could be used for instance in sleep monitoring applications.

Bioimpedance measurements may be performed with relatively simple equipment causing minimal or at least low inconvenience to the subject on which the bioimpedance measurements are performed. Use of bioimpedance measurements are therefore an especially interesting option in long-term monitoring of health and/or conditions of a subject and/or in monitoring in a home environment (outside a hospital setting).

WO 2004/112606 discloses a method of detecting sleep apnea using bioimpedance measurements including the steps applying a set of electrodes to a patient to obtain a trans-cervical bioimpedance signal from the patient, over a predetermined time period; measuring the trans-cervical bioimpedance signal to provide information about respiratory events for that patient over the predetermined time period; estimating the respiration signal using a means for estimating a respiratory signal and using the estimate of respiratory events obtained to detect presence of sleep apnea.

However, it would be desirable to obtain more comprehensive information on respiration based on bioimpedance measurements.

SUMMARY

An objective of the present inventive concept is to improve respiratory monitoring using a bioimpedance signal.

This and other objects of the present inventive concept are at least partly met by the invention as defined in the independent claims. Preferred embodiments are set out in the dependent claims.

According to a first aspect, there is provided a system for respiratory monitoring of a subject; said system comprising: a bioimpedance measurement sensor, which is configured for arrangement in relation to the subject for acquiring a bioimpedance signal; and a processing unit, which is configured to receive the acquired bioimpedance signal and receive a reference signal, the reference signal representing a respiratory effort of the subject or a respiratory airflow at a time of bioimpedance signal acquirement, the processing unit being further configured to divide the bioimpedance signal into an effort component representing a respiratory effort of the subject and a flow component representing a respiratory airflow of the subject based on the received bioimpedance signal and the received reference signal.

The system is configured to acquire a bioimpedance signal which comprises both an effort component representing a respiratory effort and a flow component representing a respiratory airflow. However, in order to better analyze the respiration of a subject, a processing unit of the system is configured to receive both the acquired bioimpedance signal and a reference signal. The processing unit may thus divide the bioimpedance signal into both an effort component and a flow component, such that the acquired bioimpedance signal may provide both a representation of respiratory effort and a representation of respiratory airflow.

The processing unit may output the effort component and the flow component, e.g. to allow further analysis of the components or to allow the effort component and the flow component to be displayed. This enables more detailed analysis of the respiration of the subject, either by automated analysis of the components, e.g. for feature extraction, or by manual analysis of the displayed components.

When a bioimpedance measurement is performed based on electrodes arranged on a thorax of a subject, chest expansion may cause a change in a current path between the electrodes, such that the bioimpedance is changed in relation to a respiratory effort. Also, air has a different impedance than tissue. As an amount of air present in the lungs varies during a respiratory cycle, the bioimpedance is also changed in relation to respiratory airflow. Thus, the bioimpedance measurement sensor may be configured for arrangement on the thorax of the subject in order to allow acquisition of a bioimpedance signal which holds information of both respiratory effort and respiratory airflow.

The bioimpedance measurement sensor may be configured for arrangement on the subject, whereby the bioimpedance measurement sensor may be configured for direct contact with the skin of the subject.

However, the bioimpedance measurement sensor may alternatively be configured for arrangement in relation to the subject so as to acquire a bioimpedance signal in a non-contact relation with the subject, e.g. using a capacitive coupling between the bioimpedance measurement sensor and the subject. For instance, the bioimpedance measurement sensor may be configured to be embedded in a bed, such as in a mattress, for acquiring of a bioimpedance signal of a subject lying in the bed. Similarly, the bioimpedance measurement sensor may be embedded in a chair or seat or in clothing that is worn by the subject.

The representations of respiratory effort and respiratory airflow may be used for analysis of respiratory action of the subject. Further, the representations of respiratory effort and respiratory airflow may be used for detection of respiratory events and for differentiation between respiratory events. For instance, differentiation may be made between two or more of obstructive sleep apnea (OSA), central sleep apnea (CSA), obstructive hypopnea, and central hypopnea.

The processing unit may be configured to receive the acquired bioimpedance signal and the reference signal in real-time, such that the processing unit may process the signals and output the effort component and the flow component in real time.

However, according to an alternative, the processing unit may perform processing of the bioimpedance signal at any time in relation to the acquiring of the bioimpedance signal and the reference signal. For instance, the bioimpedance signal and the reference signal may be acquired and gathered during a certain time period, e.g. night's sleep of the subject. The signals for the entire time period may then be provided to the processing unit, which may synchronize the bioimpedance signal with the reference signal and then process the signals to output the effort component and the flow component. The processing unit may be arranged anywhere, such as making use of processing "in the cloud".

The bioimpedance signal (and the reference signal) may be separated into sequential portions of the signal. Each portion may be separately processed for dividing the bioimpedance signal into the effort component and the flow component. However, information from previous portions may also be used for dividing the bioimpedance signal. The separation of the signal into sequential portions may be based on a change in conditions of acquiring the signal, such as the subject changing posture, or a constant length of the portions may be used.

In a further alternative, an entire time period, during which the bioimpedance signal is acquired, is commonly handled, using an assumption that the respective contributions of respiratory effort and respiratory flow may be considered constant during the entire time period.

According to an embodiment, the system further comprises a reference measurement sensor, which is configured for arrangement in relation to the subject for acquiring a reference signal representing a respiratory effort of the subject or a respiratory airflow of the subject.

As for the bioimpedance measurement sensor, the reference measurement sensor may be configured for arrangement on the subject for acquiring the reference signal, but alternatively the reference measurement sensor may be configured for arrangement in relation to the subject so as to allow the reference signal to be acquired without the reference measurement sensor being in direct contact with the subject.

Thus, the system may include a reference measurement sensor for acquiring the reference signal. Hence, the system may be provided as a prepared kit of parts, which are connected by wired or wireless connection and set up for communicating signals between different parts in the system. Thus, a user may immediately start using the system, without need of connecting parts of the system to external units, which may be provided by other vendors.

However, it should be realized that parts of the system may be provided from different vendors, such that a user may assemble the system and connect different parts to each other for e.g. providing communication of signals between different parts. Further, if the processing unit does not process the signals in real-time, the processing unit may separately receive the bioimpedance signal and the reference signal, requiring minimal set-up of the system.

According to an embodiment, the reference measurement sensor is configured to acquire a reference signal representing a respiratory effort of the subject.

This implies that the reference measurement sensor may provide information which may represent respiration mainly in terms of respiratory effort, isolated from respiratory airflow.

The reference measurement sensor configured to acquire a reference signal representing a respiratory effort may be any sensor which may be configured to acquire a representation of the respiratory effort. For instance, reference measurement sensor may include an oesophageal manometer, a respiratory inductance plethysmography (RIP) belt, a thoracoabdominal polyvinylene fluoride (PVDF) belt, an accelerometer, or an electromyograph (EMG) sensor.

The reference signal representing respiratory effort may alternatively be acquired using a sensor which is not in direct contact with the subject, but may detect movement of the chest of the subject as a measure of respiratory effort. For instance, a sensor acquiring a radar signal interacting with the subject, a camera imaging the subject or a pressure sensor may be used. The reference measurement sensor may thus e.g. be configured to be embedded in a bed/chair in which the subject lies/sits, or the reference measurement sensor may be mounted in a predetermined relation to the bed/chair.

According to an embodiment, the processing unit is configured to receive the acquired reference signal representing the respiratory effort of the subject and wherein the processing unit is configured to determine an estimation of the effort component based on the acquired bioimpedance signal and the acquired reference signal and to determine an estimation of the flow component based on the determined estimation of the effort component and the acquired bioimpedance signal.

This implies that the processing unit may use the reference signal as an estimate of a contribution of respiratory effort in the received bioimpedance signal. The reference signal may be used for deriving an estimate of the respiratory airflow as a flow component based on the bioimpedance signal and also deriving an estimate of the respiratory effort as an effort component similar to the respiratory effort provided by the reference signal.

According to an embodiment, the reference measurement sensor is configured to acquire a reference signal representing a respiratory airflow of the subject.

This implies that the reference measurement sensor may provide information which may represent respiration mainly in terms of respiratory airflow, isolated from respiratory effort.

The reference measurement sensor configured to acquire a reference signal representing a respiratory airflow may be any sensor which may be configured to acquire a representation of the respiratory airflow. For instance, reference measurement sensor may include an oro-nasal thermal sensor, such as a thermistor, a polyvinylene fluoride sensor, or a thermocouple, a nasal pressure transducer, a pneumotachograph sensor, or a spirometer.

According to an embodiment, the processing unit is configured to receive the acquired reference signal representing the respiratory airflow of the subject and wherein the processing unit is configured to determine an estimation of the flow component based on the acquired bioimpedance signal and the acquired reference signal and to determine an estimation of the effort component based on the determined estimation of the flow component and the acquired bioimpedance signal.

This implies that the processing unit may use the reference signal as an estimate of a contribution of respiratory airflow in the received bioimpedance signal. The reference signal may be used for deriving an estimate of the respiratory effort as an effort component based on the bioimpedance signal and also deriving an estimate of the respiratory airflow as a flow component similar to the respiratory airflow provided by the reference signal.

According to an embodiment, the reference signal is a first reference signal and wherein the processing unit is further configured to receive a second reference signal, the second reference signal representing a respiratory effort of the subject or representing a respiratory airflow of the subject.

This implies that the processing unit may be configured to receive a plurality of reference signals, such as two or more reference signals.

The reference signals may all relate to a same type of respiratory information. Hence, the reference signals may all represent a respiratory effort or may all represent a respiratory airflow. However, the first reference signal may represent a respiratory effort, whereas the second reference signal may represent respiratory airflow.

The processing unit may use one or more representations of respiratory effort and/or respiratory airflow in combination with the bioimpedance signal in order to divide the bioimpedance signal into the effort component and the flow component. If reference signals representing both respiratory effort and respiratory airflow are available, the reference signals may be weighted in relation to the bioimpedance signal in order to determine the effort component and the flow component. For instance, if the reference signals representing respiratory effort and respiratory airflow are not consistent with the bioimpedance signal having a contribution of both effort and airflow, accuracy of each of the signals may be taken into account in order to form the effort component and the flow component.

Reference signals representing respiratory effort may be combined to form a single signal representing respiratory effort, which may be used with processing of the bioimpedance signal. The forming of a single signal may be realized as applying a function on the reference signals, e.g. taking a (weighted) average of the reference signals, or by selecting one of the reference signals, e.g. a signal with highest reliability/accuracy.

Similarly, reference signals representing respiratory airflow may be combined to form a single signal representing respiratory airflow, which may be used with processing of the bioimpedance signal. The forming of a single signal may be realized as applying a function on the reference signals, e.g. taking a (weighted) average of the reference signals, or by selecting one of the reference signals, e.g. a signal with highest reliability/accuracy.

According to an embodiment, the processing unit is further configured to receive a respiratory event signal, which indicates abnormal respiration, wherein the processing unit is configured to divide the bioimpedance signal into the effort component and the flow component further based on the respiratory event signal.

Respiratory events may be associated with respiratory airflow or respiratory airflow and respiratory effort being impaired. Thus, knowledge of occurrence of a respiratory event may be used for drawing conclusions on contribution of an effort component and/or a flow component in the bioimpedance signal. This implies that a simplified algorithm for dividing the bioimpedance signal into the effort component and the flow component may be used during periods of occurrence of a respiratory event.

As used herein, a respiratory event may refer to cessation of respiration (apnea) or abnormally shallow breathing (hypopnea). The respiratory event may be due to a reduction or termination in respiratory airflow, which may or may not be also associated with a reduction or termination in respiratory effort.

The respiratory event signal may provide an indication that a respiratory event is occurring. In addition, the respiratory event signal may or may not provide an indication of a type of respiratory event.

The respiratory event signal may be provided based on processing of one or more of the bioimpedance signal and/or the reference signal. Hence, the bioimpedance signal in combination with the reference signal may be processed, e.g. by a respiratory event detection unit, for detecting occurrence of a respiratory event. The detected occurrence may be transferred in form a respiratory event signal to the processing unit, which may use the information when the bioimpedance signal is to be divided into the effort component and the flow component. Alternatively, the reference signal may be processed for detecting occurrence of a respiratory event.

According to yet another alternative, the processing unit may receive a respiratory event signal from a separate unit which may be configured to detect respiratory events, e.g. based on further measurements being performed on the subject. In fact, the respiratory event signal may even be provided through manual annotation, e.g. by a nurse, of respiratory events during monitoring of respiration of a subject.

According to an embodiment, the processing unit is configured to apply a blind source separation algorithm on the bioimpedance signal for dividing the bioimpedance signal into the effort component and the flow component.

This implies that the mixing of respiratory effort and respiratory airflow in the bioimpedance signal may be separated in a robust manner into the effort component and the flow component. The blind source separation algorithm may use the reference signal(s) as observable variable(s) for estimating the underlying effort component and flow component in the bioimpedance signal.

The blind source separation algorithm may use a linear model to represent the signals. However, the blind source separation algorithm may alternatively use a non-linear model, which enable more correct separation of the effort component and the flow component.

According to another embodiment, the processing unit is configured to use an adaptive filter for dividing the bioimpedance signal into the effort component and the flow component.

Use of an adaptive filter may enable less complex processing of the bioimpedance signal compared to use of a blind source separation algorithm. However, the blind source separation algorithm may be able to provide more correct separation of the effort component and the flow component.

The adaptive filter may use e.g. a Wiener or a Kalman filter.

According to an embodiment, the processing unit is configured to preprocess the bioimpedance signal before dividing the bioimpedance signal into the effort component and the flow component.

The preprocessing of the bioimpedance signal may be configured to filter the bioimpedance signal, e.g. for noise removal and/or for removing contribution of cardiac activity in the bioimpedance signal.

The preprocessing of the bioimpedance signal may also or alternatively be configured to perform one or more of data cleaning, resampling, and shifting of the bioimpedance signal.

It should be realized that the processing unit may be provided as a single processor, which may execute one or more processing threads for providing processing of the received signals. However, the processing unit may also be distributed in a plurality of physical units. For instance, the preprocessing may be performed on a processor arranged in a housing in which the bioimpedance measurement sensor is placed, which processor may transfer the preprocessed bioimpedance signal to a central processor, which may be configured to also receive the reference signal and divides the bioimpedance signal into the effort component and the flow component.

According to an embodiment, the bioimpedance measurement sensor is arranged on a carrier configured for being arranged on a thorax region of the subject.

The carrier may for instance comprise an adhesive patch, a textile/garment being worn by the subject, or a belt, which may be configured to be attached around a torso of the subject.

In particular, an adhesive patch may enable firm and well-controlled placement of the bioimpedance measurement sensor on the thorax region of the subject.

The processing unit may be arranged on the carrier with the bioimpedance measurement sensor. The processing unit may thus be configured to receive the bioimpedance signal directly from the bioimpedance measurement sensor.

The reference measurement sensor may also be arranged on the carrier. This may be particularly useful, e.g. if the reference measurement sensor is arranged to acquire a reference signal representing a respiratory effort, as such a reference signal may be advantageously acquired from a position on the thorax region.

However, the processing unit may alternatively be arranged in a central unit, which may or may not be worn by the subject. The central unit may be connected by wires or wirelessly to the bioimpedance measurement sensor and the reference measurement sensor for receiving the bioimpedance signal and the reference signal.

The system may thus comprise a plurality of units which may include a plurality of units separately attachable to different body parts of the subject. The processing unit may be arranged in one of these units which is attached to the subject or in a central unit, as described above.

It should also be realized that the system may comprise one or more communication units, which may communicate the bioimpedance signal and the reference signal, e.g. via a telecommunication or computer network, to a processing unit, which may be arranged in a remote location. The bioimpedance signal and the reference signal may be communicated jointly or separately to the processing unit. Thus, the processing unit may even be arranged "in the cloud".

According to an embodiment, the bioimpedance measurement sensor comprises at least two or at least four electrodes and is configured for bipolar or tetrapolar measurement of the bioimpedance.

In a bipolar measurement, the same electrodes may be used both for providing a stimulation signal and for acquiring the bioimpedance signal. This implies that the bioimpedance measurement sensor may comprise few electrodes.

In a tetrapolar measurement, two electrodes are used for providing a stimulation signal and two other electrodes are used for acquiring the bioimpedance signal.

According to a second aspect, there is provided a method for respiratory monitoring of a subject, said method comprising: receiving an acquired bioimpedance signal representing a bioimpedance of the subject; receiving an acquired reference signal representing a respiratory effort of the subject or representing a respiratory airflow of the subject, wherein the bioimpedance signal and the reference signal have been acquired simultaneously; and dividing the bioimpedance signal into an effort component representing a respiratory effort of the subject and a flow component representing a respiratory airflow of the subject based on the received bioimpedance signal and the received reference signal.

Effects and features of this second aspect are largely analogous to those described above in connection with the first aspect. Embodiments mentioned in relation to the first aspect are largely compatible with the second aspect.

The receiving of a bioimpedance signal and a reference signal which have been simultaneously acquired from a subject is used for dividing the bioimpedance signal into an effort component and a flow component so as to provide comprehensive information of respiration of the subject.

According to a third aspect, there is provided a computer program product comprising a computer-readable medium storing computer-readable instructions such that when executed on a processing unit the computer program product will cause the processing unit to perform the method according to the second aspect.

Effects and features of this third aspect are largely analogous to those described above in connection with the first and second aspects. Embodiments mentioned in relation to the first and second aspects are largely compatible with the third aspect.

The computer program product may thus control a processing unit to perform the method for respiratory monitoring such that both an effort component and a flow component may be provided from the bioimpedance signal allowing detailed analysis of the respiration of the subject.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1:
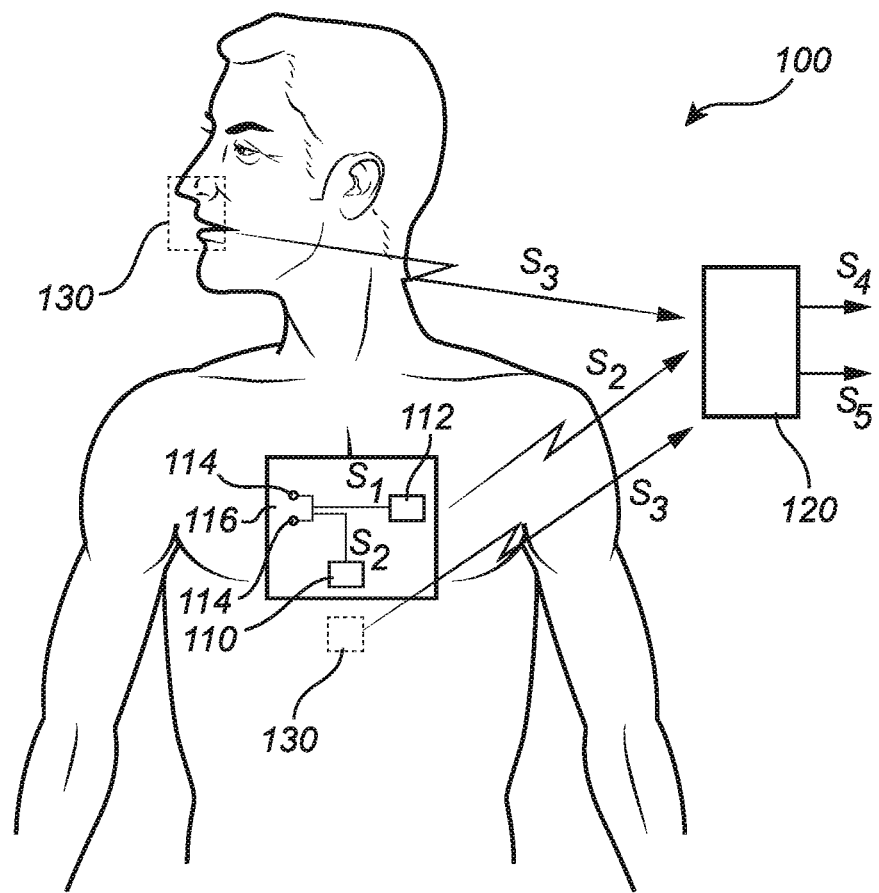
FIG. 1 is a schematic view of a system according to an embodiment.

FIG. 1 illustrates a system 100 for respiratory monitoring of a subject. The system 100 may be configured to generate a current signal S1 that is to be applied to a subject and may comprise a bioimpedance measurement sensor 110 to measure a bioimpedance signal S2 providing information of the bioimpedance of the subject, which may be further processed for monitoring respiration of the subject. The bioimpedance signal S2 may be provided together with a reference signal S3 to a processing unit 120 which may divide the bioimpedance signal S2 into an effort component S4 and a flow component S5.

As shown in FIG. 1, the system 100 comprises a current signal injection module 112. The current signal injection module 112 may be configured to generate and output the current signal S1, which is to be applied to the subject. The current signal injection module 112 may comprise a current source for generating a current signal S1. The current signal injection module 112 may be configured to output an AC current signal.

The system 100 further comprises a bioimpedance measurement sensor 110. The bioimpedance measurement sensor 110 may be configured to receive voltage input signals representing a voltage generated by the current signal S1 applied to the subject. The bioimpedance measurement sensor 110 may be configured to extract a measured bioimpedance signal S2 from the received voltage input signals.

The bioimpedance measurement sensor 110 may be configured to process the received voltage input signals, e.g. by filtering the input signals, in order to extract relevant information.

The bioimpedance measurement sensor 110 may comprise two or more electrodes 114, which may be arranged to be in contact with skin of the subject. The electrodes 114 may be connected to the current signal injection module 112 to receive the current signal S1 and provide the current signal through tissue of the subject. The electrodes 114 may also be connected to the bioimpedance measurement sensor 110 for providing voltage input signals that may be used for measuring the bioimpedance signal S2.

The electrodes 114 may be arranged in a bipolar arrangement, wherein the same electrodes 114 are used for providing the current signal S1 to the subject and for acquiring the voltage input signals. However, the electrodes 114 may alternatively be arranged in a tetrapolar arrangement, wherein two electrodes are used for providing the current signal S1 to the subject and two other electrodes are used for acquiring the voltage input signals.

More than two (or four) electrodes 114 may be provided, which may allow selection of which electrodes 114 to be used in a measurement, so that electrodes 114 providing highest quality bioimpedance signal S2 may be selected. The selection of which electrodes 114 to be used may be performed in set-up of the system 100 or may be dynamically changed during signal acquisition e.g. when conditions for acquiring the bioimpedance signal change.

The bioimpedance measurement sensor 110 with electrodes 114 may be configured to be attached on a thorax region of the subject. The bioimpedance measurement sensor 110 may be arranged on a carrier 116 configured for being arranged on a thorax region of the subject, wherein the electrodes 114 may be mounted to be exposed on the carrier 116, such that the electrodes 114 may be arranged in contact with the skin of the subject.

The carrier 116 may for instance comprise an adhesive patch, a textile/garment being worn by the subject, or a belt, which may be configured to be attached around the torso of the subject.

When a bioimpedance measurement is performed based on electrodes 114 arranged on the thorax of a subject, chest expansion may cause a change in a current path between the electrodes 114, such that the bioimpedance is changed in relation to a respiratory effort. Also, air has a different impedance than tissue. As an amount of air present in the lungs varies during a respiratory cycle, the bioimpedance is also changed in relation to respiratory airflow. Thus, the bioimpedance measurement sensor 110 may be configured for acquisition of a bioimpedance signal S2 which holds information of both respiratory effort and respiratory airflow.

The processing unit 120 may be configured to receive the bioimpedance signal S2 from the bioimpedance measurement sensor 110. The processing unit 120 may further be configured to receive a reference signal S3 from a reference measurement sensor 130.

The reference signal S3 may be acquired so as to isolate respiratory effort from respiratory airflow, e.g. by using a sensor which is placed or configured for acquiring a signal which is only affected by either respiratory effort or respiratory airflow. Hence, the reference signal S3 may represent respiratory effort or respiratory airflow.

The processing unit 120 may be configured to process the bioimpedance signal S2 and the reference signal S3 so as to divide the bioimpedance signal S2 into an effort component S4 representing respiratory effort and a flow component S5 representing respiratory airflow.

The processing unit 120 may be implemented in hardware, or as any combination of software and hardware. The processing unit 120 may, for instance, be implemented as software being executed on a general-purpose computer. The system 100 may thus comprise one or more physical processors, such as a central processing unit (CPU), which may execute the instructions of one or more computer programs in order to implement functionality of the processing unit 120. Thus, the system 120 may comprise a single processing unit, which may provide a plurality of functionalities e.g. as separate threads within the processing unit 120.

The processing unit 120 may alternatively be implemented as firmware arranged e.g. in an embedded system, or as a specifically designed processing unit, such as an Application-Specific Integrated Circuit (ASIC) or a Field-Programmable Gate Array (FPGA).

The reference measurement sensor 130 may be part of and may be delivered with the system 100. The system 100 may thus be set-up for communication between the reference measurement sensor 130 and the processing unit 120.

However, the reference measurement sensor 130 may alternatively be separately delivered, e.g. by a different vendor than the vendor providing the system 100. A user may thus connect the reference measurement sensor 130 to the processing unit 120, e.g. by attaching a wire between the reference measurement sensor 130 and a port in a housing in which the processing unit 120 is arranged, whereby the processing unit 120 and the reference measurement sensor 130 may then exchange set-up messages for automatically setting up communication between each other. Alternatively, a user may initiate a discovery procedure for allowing a wireless communication between the reference measurement sensor 130 and the processing unit 120 to be established and again for automatically setting up communication between the reference measurement sensor 130 and the processing unit 120.

In a further alternative, the reference measurement sensor 130 and the bioimpedance measurement sensor 110 may be configured to separately communicate the reference signal S3 and the bioimpedance signal S2 to a remotely arranged processing unit 120, e.g. a processing unit 120 arranged "in the cloud". The signals may be communicated after an entire period of gathering the signals, such as signals acquired during a night's sleep of the subject. The processing unit 120 may then synchronize the signals before processing.

A reference measurement sensor 130 configured to acquire a reference signal representing a respiratory effort may be any sensor which may be configured to acquire a representation of the respiratory effort. For instance, the reference measurement sensor 130 may include an oesophageal manometer, a respiratory inductance plethysmography (RIP) belt, a thoracoabdominal polyvinylene fluoride (PVDF) belt, an accelerometer, or an electromyograph (EMG) sensor.

A reference measurement sensor 130 configured to acquire a reference signal representing a respiratory airflow may be any sensor which may be configured to acquire a representation of the respiratory airflow. For instance, reference measurement sensor may include an oro-nasal thermal sensor, such as a thermistor, a polyvinylene fluoride sensor, or a thermocouple, a nasal pressure transducer, a pneumotachograph sensor, or a spirometer.

The processing unit 120 may be configured to receive reference signals S3 from a plurality of reference measurement sensors 130. The plurality of reference measurement sensors 130 may comprise only sensors configured to acquire a reference signal S3 representing respiratory effort, only sensors configured to acquire a reference signal S3 representing respiratory airflow, or one or more sensors configured to acquire a reference signal S3 representing respiratory effort combined with one or more sensors configured to acquire a reference signal S3 representing respiratory airflow. To illustrate these options, reference measurement sensors 130 are indicated by dashed lines in FIG. 1.

The system 100 may comprise one or more housings, in which the bioimpedance measurement sensor 110, the processing unit 120 and the reference measurement sensor 130 may be arranged. The housings may be connected by wires for allowing communication between the sensors and the processing unit 120. Alternatively, one or more of the sensors 110, 130 and the processing unit 120 may be set up for wireless communication. The system 100 may thus be delivered to be ready to use, e.g. in a single package with all parts of the system 100 already set up to communicate with each other.

The processing unit 120 may be arranged in a housing on the carrier 116. The reference measurement sensor 130 may also be arranged on the same carrier 116.

However, in an alternative embodiment, the processing unit 120 may be arranged in a central housing, which may be separate from the carrier 116. The central housing may further comprise an output port for connection to an external unit, which may receive the effort component S4 and the flow component S5 for further processing of the components. Alternatively or additionally, the central housing may comprise a communication unit for wireless communication of the effort component S4 and the flow component S5 to the external unit.

The central housing may also be connected to a display for enabling the effort component S4 and the flow component S5 to be output on the display. Also, the reference signal may be output on the display S3. This may allow a physician, nurse or any other person, to manually inspect signals representing respiration of the subject, e.g. for manual analysis of the respiration.

Figure 2:
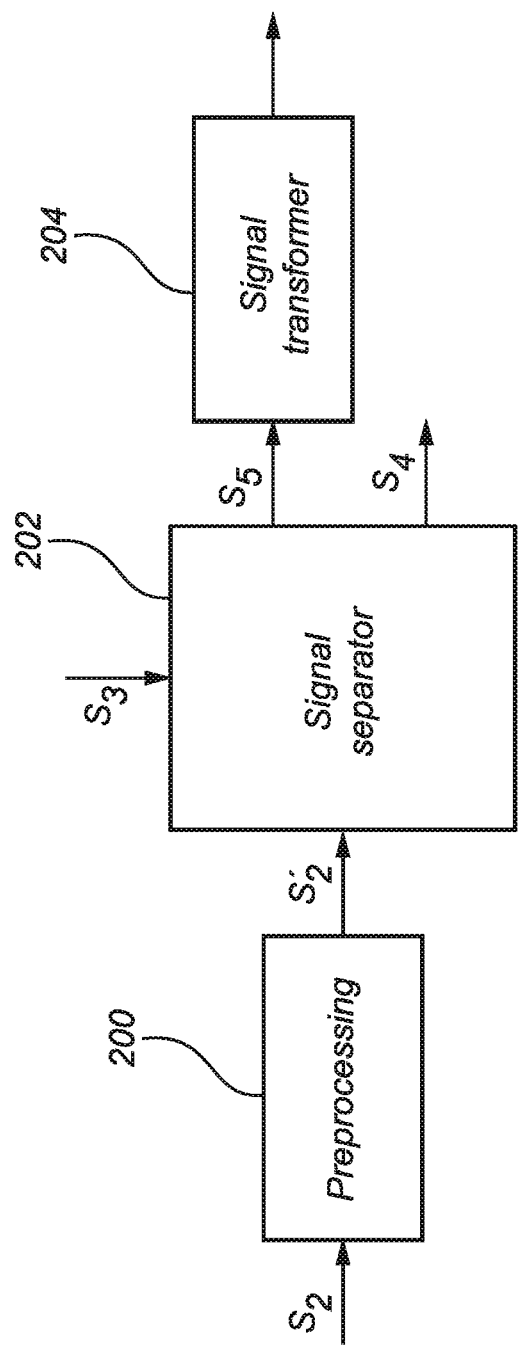
FIG. 2 is a schematic view of processing of a bioimpedance signal to divide the bioimpedance signal into an effort component and a flow component.

Referring now to FIG. 2, processing of the bioimpedance signal S2 and the reference signal(s) S3 will be further described.

The bioimpedance signal S2 may first be provided to a preprocessing unit 200. The preprocessing unit 200 may apply preprocessing of the bioimpedance signal S2, which may be configured to filter the bioimpedance signal S2, e.g. for noise removal and/or for removing contribution of cardiac activity in the bioimpedance signal S2.

The preprocessing of the bioimpedance signal S2 may also or alternatively be configured to perform one or more of data cleaning, resampling, and shifting of the bioimpedance signal S2.

The preprocessing unit 200 may output a cleaned bioimpedance signal S2' which is a combined representation of respiratory effort and respiratory airflow.

The cleaned bioimpedance signal S2' may be provided to a signal separator 202. The signal separator 202 may also receive a reference signal S3 from a reference measurement sensor 130. The reference signal S3 may also have been subject to preprocessing, e.g. to remove noise, before being received by the signal separator 202.

The signal separator 202 may or may not first apply a transformation to the bioimpedance signal S2'. As will be exemplified below, processing of the bioimpedance signal S2' may be performed directly on the bioimpedance signal S2', on a derivative Z' of the bioimpedance signal S2' or a transform using the derivative Z' and square $Z^2$ of the bioimpedance signal S2' ($Z'/Z^2$). It should also be realized that transformation of the biompedance signal S2' may also include multiplying by a constant K1 and adding another constant K2.

The signal separator 202 may then apply an algorithm for dividing the, possibly transformed, bioimpedance signal S2' into a contribution from respiratory effort and a contribution from respiratory airflow using the information in the reference signal S3.

The signal separator 202 may possibly further process the signals after dividing of the biompedance signal S2'. The signal separator 202 may then output an effort component S4, indicating contribution from respiratory effort, and a flow component S5, indicating contribution from respiratory airflow.

The contribution of respiratory airflow may optionally be provided to a signal transformer 204. The signal transformer 204 may may process the flow component S5, by integrating the flow component S5 and possibly adding a constant, in order to provide an estimated measure of lung volume The effort component S4 and the flow component S5 may further be provided to separate further processing steps, which may be specifically adapted for processing of the component received, e.g. for further cleaning the signals.

The processing made by the signal separator 202 according to a first embodiment using a blind source separation (BSS) algorithm will now be described.

In this example, a model used for representing relations between contributions of effort and airflow is described by:

$1/Z = 1/Z_l + 1/Z_c + 1/Z_n$ where
Z: combined measured bioimpedance
$Z_c$: impedance of chest wall
$Z_l$: impedance of the lungs; and
$Z_n$: impedance of other tissues and heart/blood vessels.
In addition, applying the derivatives of $Z_c$ and $Z_l$:
$Z'_c$ represents the respiratory effort and
$Z'_l$ represents the respiratory airflow.

A blind source separation algorithm may then use reference signal(s) as observable variables providing reference effort and/or reference flow. This may be used to estimate the underlying effort source and flow source signals.

Assuming preprocessing filters out unwanted noise, e.g. impedance of other tissues $Z_n$, and interference from other physiological process such as cardiac activity, the model may be described as:

$Z = Z_c * Z_l / (Z_c + Z_l)$, where Z is the observed bioimpedance.

Applying a derivative, measures of flow and effort are obtained, $Z'_l$ and $Z'_c$, which relate to a derivative of the observed bioimpedance $Z'$ as follows:

$$Z'/(Z^2)=Z'_l/(Z^2)+Z'_c/(Z_c^2).$$

The measure of flow, $Z'_l$, is a function of the flow component $s_{fl}$, a source signal that the BSS algorithm targets to estimate and separate, i.e. $Z'_l=F_l(s_{fl})$, where $F_l$ denotes the function relating $Z'_l$ to the flow component $s_{fl}$.

Similarly, the derivative measure of effort, $Z'_c$, is a function of the effort component $s_{eff}$, another source signal that the BSS algorithm targets to estimate and separate, i.e. $Z'_c=F_c(s_{eff})$, where $F_c$ denotes the function relating $Z'_c$ to the effort component $s_{eff}$.

Further, each reference signal is a transformation of the source signal, and may be represented as:

$$X_{ref,fl}=G_{fl}(s_{fl}); \text{ and } X_{ref,eff}=G_{eff}(s_{eff}),$$

where $X_{ref,fl}$ is a reference signal representing respiratory airflow and $G_{fl}$ denotes the function relating $X_{ref,fl}$ to the flow component $s_{fl}$ and where $X_{ref,eff}$ is a reference signal representing respiratory effort and $G_{eff}$ denotes the function relating $X_{ref,eff}$ to the effort component $s_{eff}$.

Blind source separation algorithms may use different approaches to extract the source signals from the observed variables.

The acquired bioimpedance signal as well as the effort component and the flow component are typically sinusoidal (having specific frequency and phase, time varying). This may be exploited by the blind source separation algorithm for simple parameterization of transformation functions to find the source signals.

If several reference signals are available, each of these may be used by the blind source separation algorithm, with a respective function relating the reference signal to the source component.

However, according to an alternative, a single reference signal may be formed based on a plurality of reference signals.

The processing made by the signal separator 202 according to a second embodiment using an adaptive filter will now be described.

In this embodiment, surrogates of the effort component and the flow component are used (i.e. signals related to the effort component and the flow component, respectively). Then, an additive model for the surrogates of effort and flow components of the bioimpedance signal may be used and less complex signal processing may be used in order to divide the bioimpedance signal into the effort component and the flow component. Thus, the processing of the signal separator 202 may be faster and may require less computer resources. However, at least in some cases, the use of the blind source separation algorithm as described in the first embodiment above may more accurately extract the effort and flow components.

In this embodiment, the relation $Z'/Z^2=Z'_c/Z_c^2+Z'_l/Z_l^2$ after appropriate preprocessing to form the bioimpedance signal $Z$ as earlier described is used.

After measurement of $Z$, a transformation of the bioimpedance signal $BioZ_t$ may be computed as $BioZ_t=Z'/Z^2$.

Further, correspondingly transformed signals of the effort component and the flow component may be used as surrogates, i.e. $Z'_l/Z_l^2$ as a surrogate for the flow component and $Z'_c/Z_c^2$ as a surrogate for the effort component, instead of the direct flow estimate ($Z'_l$) and direct effort estimate ($Z'_c$). Thus, it is possible to apply a simpler signal processing method, such as Kalman or Wiener filtering.

Figure 3:
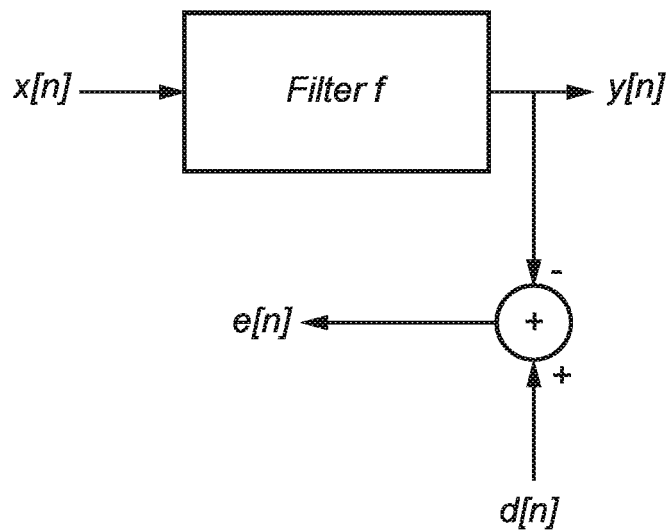
FIG. 3 is a schematic view of a Wiener filter which may be used in the processing of the bioimpedance signal.

For instance, Wiener filtering may be used as is generally illustrated in FIG. 3.

In the present case, the input signal (denoted $x[n]$ in FIG. 3) is the transformation of the bioimpedance signal, $BioZ_t$. The reference signal (denoted $d[n]$ in FIG. 3) is the reference signal received by the processing unit 120, which may be either $X_{ref,fl}$ (if a reference representing respiratory airflow is received) or $X_{ref,eff}$ (if a reference representing respiratory effort is received). The reference signal may alternatively be a transformed measure of the signal received by the processing unit, such as $X'_{ref}/X_{ref}^2$. For simplicity, only the reference signal $X_{ref,fl}$ or $X_{ref,eff}$ is considered below.

Based on this model, the Wiener filter (denoted as f) needs to be computed, such that the Wiener filter will minimize a certain cost function of the error (denoted $e[n]$ in FIG. 3). Typically, a Mean Square Error may be used as a cost function. Then, the Wiener filter is computed based on the autocorrelation (an estimate) of the input signal $BioZ_t$ and the cross-correlation (an estimate of the cross-correlation with finite samples) between $BioZ_t$ and $X_{ref,eff}$ or $X_{ref,fl}$.

Once the filter coefficients (arbitrary filter length) are computed, it is possible to obtain a component from the transformed bioimpedance signal after filtering, i.e. $BioZ_{tf}=BioZ_t*f$.

If the reference signal is a representation of respiratory effort, $X_{ref,eff}$, the filter then provides the following surrogate estimation of respiratory effort:

SurrBioZ$_{eff}$=BioZ$_{tf}$, which is a measure of $Z'_c/Z_c^2$, and which is an effort component of the transformed bioimpedance signal.

Then, it is also possible to compute the surrogate estimation of respiratory airflow as:

$$\text{SurrBioZ}_{fl}=\text{BioZ}_t-\text{BioZ}_{tf}.$$

Similarly, if the reference signal is a representation of respiratory airflow, $X_{ref,fl}$, the filter then provides the following surrogate estimation of respiratory airflow:

SurrBioZ$_{fl}$=BioZ$_{tf}$, which is a measure of $Z'_l/Z_l^2$, and which is a flow component of the transformed bioimpedance signal.

Then, it is also possible to compute the surrogate estimation of respiratory effort as:

$$\text{SurrBioZ}_{eff}=\text{BioZ}_t-\text{BioZ}_{tf}.$$

The computed surrogate estimations of respiratory effort and respiratory flow may be sufficient for signal representation, given that the surrogate estimations are proportional to the variations of chest wall impedance variations (effort) and lung impedance variations (flow). Thus, the surrogate estimations may be output as representations of effort component and flow component.

However, it is also possible to generate the estimated $Z'_l$ and $Z'_c$ signals (starting from the surrogate estimations, $Z'_l/Z_l^2$ and $Z'_c/Z_c^2$, respectively). The generation may include the following steps: integrate the surrogate estimation, remove a DC component, apply a negative inversion and derive the signal, whereby the estimated $Z'_l$ and $Z'_c$ signals may be obtained.

The extracted effort component and flow component may be used in detection of respiratory events. The effort component and the flow component may also be used in classifying of respiratory events based on an indication received that a respiratory event is occurring.

Figure 4:
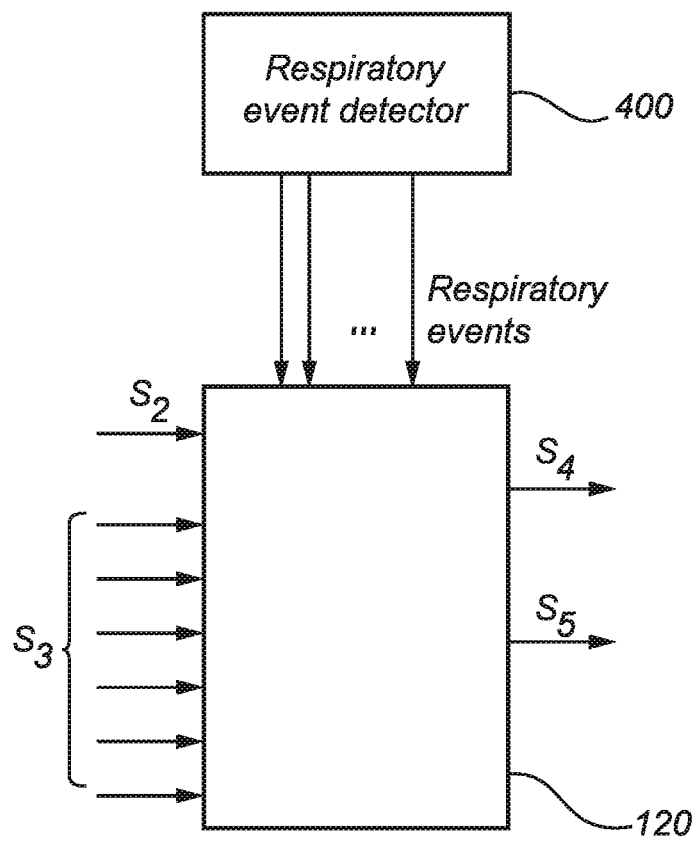
FIG. 4 is a schematic view of processing of a bioimpedance signal receiving a respiratory event signal.

As illustrated in FIG. 4, the processing unit 120 may be configured to receive a respiratory event signal, in addition to receiving reference signal(s) S3. The respiratory event signal may provide a classification into one or more categories of respiratory events and may also provide an indication of a time period during which the respiratory event occurs/occurred.

The respiratory event signal may be received from a respiratory event detector 400. The respiratory event detector 400 may process one or more of the bioimpedance signal S2, the reference signal(s) S3 or other signals in order to determine respiratory events. The respiratory event signal may alternatively be provided through manual input, e.g. by a nurse providing manual annotation of an acquired signal during respiratory monitoring.

Figure 5:
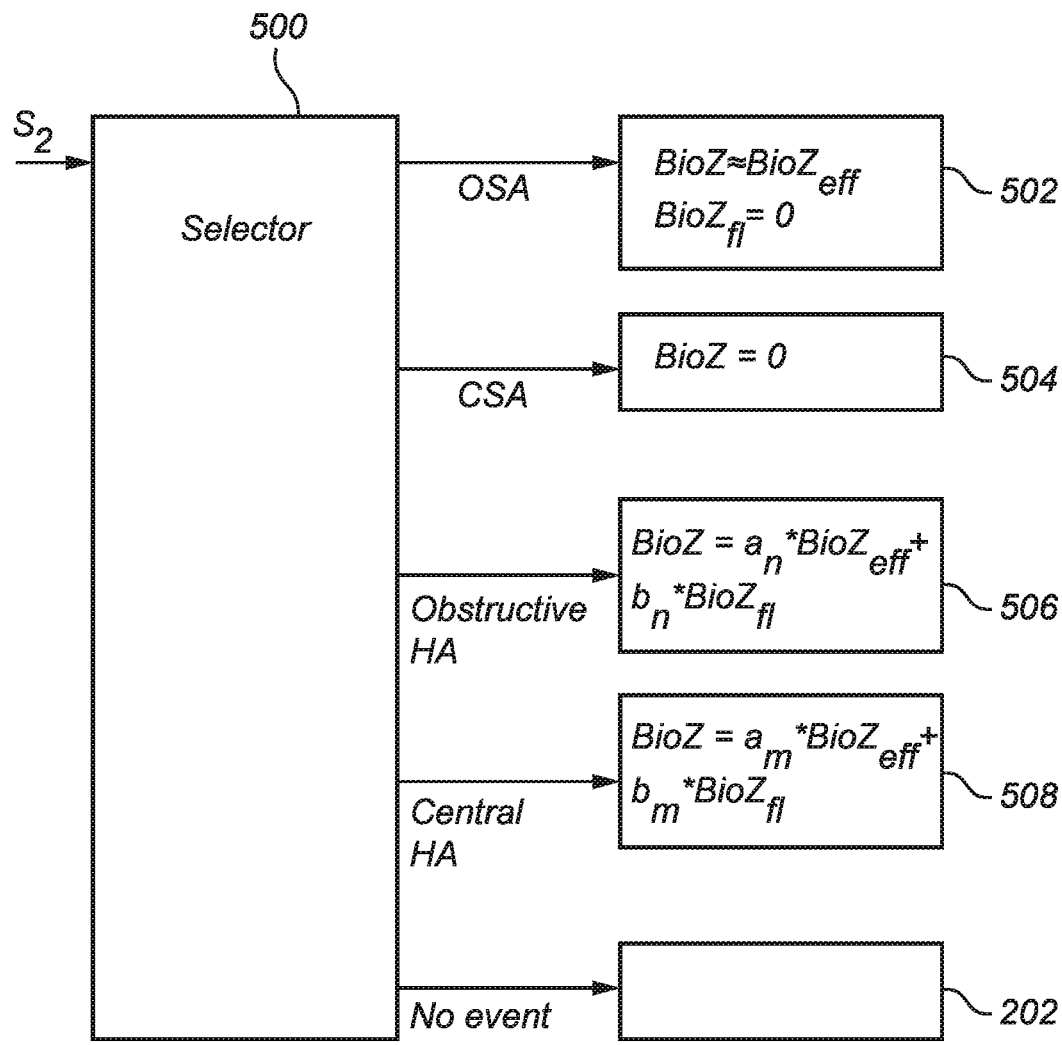
FIG. 5 is a schematic view of simplified processing of the bioimpedance signal based on occurrence of a respiratory event.

Referring now to FIG. 5, the processing of the bioimpedance signal S2 in order to divide the bioimpedance signal S2 into an effort component and a flow component may be simplified.

Thus, a selector 500 may select how the bioimpedance signal S2 is to be processed based on a type of respiratory event occurring. The selector 500 may transfer the bioimpedance signal S2 to a signal separator corresponding to the respiratory event.

If an obstructive sleep apnea (OSA) event occurs, a signal separator 502 may operate on the bioimpedance signal. Then, the bioimpedance signal, BioZ, may be considered to be equivalent to the respiratory effort component within the OSA period, i.e. BioZ≈$BioZ_{\it eff}$. The flow component, $BioZ_{\it fl}$, is in this case 0 as no airflow occurs during OSA.

The OSA periods may be used to parameterize the function $f_{\it eff}$ of respiratory effort, as $BioZ_{\it eff}=f_{\it eff}(X_{\it ref,eff})$. This may then be used outside OSA periods as well for estimating the effort component. Further, outside OSA periods, the flow component may then be estimated as $BioZ_{\it fl}=BioZ-f_{\it eff}(X_{\it ref,eff})$.

If a central sleep apnea (CSA) event occurs, neither respiratory effort nor respiratory airflow occurs. The signal separator 504 then represents the bioimpedance as BioZ=0. This is not further used for estimating flow component or effort component outside CSA periods.

If an obstructive hypopnea (HA) event occurs, a signal separator 506 may operate on the bioimpedance signal. Then, the bioimpedance signal may be represented as $BioZ=a_n*BioZ_{\it eff}+b_n*BioZ_{\it fl}$, where $b_n<b_0$, where
- $a_0$ is the weighing coefficient for the effort component in periods without respiratory events,
- $b_0$ is the weighing coefficient for the contribution of the flow component in periods without respiratory events,
- $a_n$ is the weighing coefficient for the effort component within obstructive HA periods, and
- $b_n$ is the weighing coefficient for the contribution of the flow component within obstructive HA periods.

It may be possible to make assumptions that may be used in estimation of $a_n$ and $b_n$. For instance, the coefficient for effort component $a_n$ may be set to equal the coefficient $a_0$. The coefficient for flow component $b_0$ could be chosen e.g. based on a range assumption, e.g. $0.1*b_0<=b_n<=0.3*b_0$. A relation in this range may be used, e.g. $b_n=0.2*b_0$.

If a central hypopnea (HA) event occurs, a signal separator 508 may operate on the bioimpedance signal. Then, the bioimpedance signal may be represented as $BioZ=a_m*BioZ_{\it eff}+b_m*BioZ_{\it fl}$, where $b_m<b_0$ and $a_m<a_0$, where
- $a_m$ is the weighing coefficient for the effort component within central HA periods, and
- $b_0$ is the weighing coefficient for the contribution of the flow component within central HA periods.

As for the discussion with regard to obstructive HA events, assumptions could be used for relating the coefficients for effort component and flow component in periods without respiratory events to the coefficients determined in the central HA periods.

If there is no event occurring, the signal separator 202 described above with reference to FIG. 2 may operate on the bioimpedance signal.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A system for respiratory monitoring of a subject, said system comprising:
   a bioimpedance measurement sensor, which is configured for arrangement in relation to the subject for acquiring a bioimpedance signal; and
   a processing unit, which is configured to receive the acquired bioimpedance signal and receive a reference signal, the reference signal representing an amount of respiratory effort of the subject or an amount of respiratory airflow at a time of bioimpedance signal acquirement, the processing unit being further configured to process the bioimpedance signal using information in the received reference signal to separate the bioimpedance signal into an effort signal component and a flow signal component, the effort signal component representing the respiratory effort of the subject, and the flow signal component representing the respiratory airflow of the subject,
   wherein the bioimpedance measurement sensor is arranged on a carrier configured for being arranged on a region of the body of the subject.

2. The system according to claim 1, further comprising a reference measurement sensor, which is configured for arrangement in relation to the subject for acquiring the reference signal representing the amount of respiratory effort of the subject or the amount of respiratory airflow of the subject.

3. The system according to claim 2, wherein the reference measurement sensor is configured to acquire the reference signal representing the amount of respiratory effort of the subject.

4. The system according to claim 3, wherein the processing unit is configured to receive the acquired reference signal representing the amount of respiratory effort of the subject and wherein the processing unit is configured to determine an estimation of the effort signal component based on the acquired bioimpedance signal and the acquired reference signal and to determine an estimation of the flow signal component based on the determined estimation of the effort signal component and the acquired bioimpedance signal.

5. The system according to claim 2, wherein the reference measurement sensor is configured to acquire the reference signal representing the amount of respiratory airflow of the subject.

6. The system according to claim 5, wherein the processing unit is configured to receive the acquired reference signal representing the amount of respiratory airflow of the subject and wherein the processing unit is configured to determine an estimation of the flow signal component based on the acquired bioimpedance signal and the acquired reference signal and to determine an estimation of the effort signal component based on the determined estimation of the flow signal component and the acquired bioimpedance signal.

7. The system according to claim 1, wherein the reference signal is a first reference signal and wherein the processing unit is further configured to receive a second reference signal, the second reference signal representing the amount of the respiratory effort of the subject or representing the amount of the respiratory airflow of the subject.

8. The system according to claim 1, wherein the processing unit is further configured to receive a respiratory event signal, wherein the processing unit is configured to divide the bioimpedance signal into the effort signal component and the flow signal component further based on the respiratory event signal.

9. The system according to claim 1, wherein the processing unit is configured to apply a blind source separation algorithm on the bioimpedance signal for dividing the bioimpedance signal into the effort signal component and the flow signal component.

10. The system according to claim 9, wherein the processing unit is configured to use the received reference signal as observable variables providing reference effort or reference flow.

11. The system according to claim 1, wherein the processing unit is configured to use an adaptive filter for dividing the bioimpedance signal into the effort signal component and the flow signal component.

12. The system according to claim 11, wherein the processing unit is configured to use the received reference signal as input for comparing a filtered signal to the received reference signal for obtaining the effort signal component or the flow signal component from the bioimpedance signal.

13. The system according to claim 1, wherein the processing unit is configured to preprocess the bioimpedance signal before dividing the bioimpedance signal into the effort signal component and the flow signal component.

14. The system according to claim 1, wherein the region of the body of the subject includes a thorax region of the subject.

15. The system according to claim 1, wherein the bioimpedance measurement sensor comprises two electrodes configured for bipolar measurement of the bioimpedance or four electrodes configured for tetrapolar measurement of the bioimpedance.

16. A method for respiratory monitoring of a subject, said method comprising:
- receiving an acquired bioimpedance signal representing a bioimpedance of the subject, wherein the bioimpedance signal is acquired by a bioimpedance measurement sensor arranged on a carrier configured for being arranged on a region of the body of the subject;
- receiving an acquired reference signal representing an amount of respiratory effort of the subject or representing an amount of respiratory airflow of the subject, wherein the bioimpedance signal and the reference signal have been acquired simultaneously; and
- processing the bioimpedance signal using information in the received reference signal to separate the bioimpedance signal into an effort signal component and a flow signal component, the effort signal component representing the respiratory effort of the subject, and the flow signal component representing the respiratory airflow of the subject.

17. A computer program product comprising a computer-readable medium storing computer-readable instructions such that when executed on a processing unit the computer program product will cause the processing unit to perform the method according to claim 16.

* * * * *